United States Patent [19]
Winterbottom et al.

[11] Patent Number: 5,756,361
[45] Date of Patent: May 26, 1998

[54] SCREENING METHOD FOR PERIODONTAL DISEASE

[75] Inventors: Neil Winterbottom, San Mateo; Viola T. Kung, Menlo Park; Baltazar Gomez, Fremont, all of Calif.; F. Michael Eggert, Edmonton, Canada

[73] Assignee: Metra Biosystems, Inc., Mountain View, Calif.

[21] Appl. No.: 303,047

[22] Filed: Sep. 8, 1994

Related U.S. Application Data

[63] Continuation-in-part of Ser. No. 209,924, Mar. 11, 1994, abandoned, Ser. No. 140,284, Oct. 20, 1993, abandoned, and Ser. No. 992,936, Dec. 17, 1992, abandoned.

[51] Int. Cl.$^6$ ................................................ G01N 33/53
[52] U.S. Cl. ........................ 436/518; 436/528; 436/531; 436/547; 436/548; 436/811; 436/815; 435/7.9; 435/7.92; 435/7.93
[58] Field of Search ...................... 436/518, 528, 436/531, 547, 548, 811, 815; 435/7.9, 7.92, 7.93

[56] References Cited

U.S. PATENT DOCUMENTS 5,516,699   5/1996   Giannobile et al. .................. 436/96

FOREIGN PATENT DOCUMENTS

| 556 152A1 | 8/1993 | European Pat. Off. |
| WO 91/10141 | 7/1991 | WIPO |
| WO 94/03814 | 2/1994 | WIPO |
| WO 94/14072 | 6/1994 | WIPO |
| WO 95/22763 | 8/1995 | WIPO |

OTHER PUBLICATIONS

Hanson et al., "A Specific Immunoassay for Monitoring Human Bone Resorption: Quantitation of Type I Collagen Crosslinked N-Telopeptides in Urine," *Journal of Bone and Mineral Research*, vol. 7, No. 11, pp. 1251–1258 (1992).

Seyedin et al., "Immunoassay for Urinary Pyridinoline: The New Marker of Bone Resorption." *Journal of Bone and Mineral Research*, vol. 8, No. 5, pp. 635–641 (1993).

Talonpoika et al., "Type I collagen carboxyterminal telopeptide in human gingival crevicular fluid in different clinical conditions and after periodontal treatment," *Journal of Clinical Periodontology*, vol. 21, pp. 320–326 (1994).

Robinson et al., "Connective tissue components of the periodontium as markers of periodontal destruction. A critical approach.", *Journal of Dental Research*, vol. 71, Special Issue, IADR Abstracts, p. 747, Abstract 1850 (1992).

Waterhouse et al., "Introduction and Biological Basis", in *Oral Manifestations of Systemic Disease*, Jones et al., eds. W.B. Saunders Company Ltd., Philadelphia (1980).

Mandel et al., "The salivary secretions in health and disease," *Oral Sci. Rev.*, vol. 8, pp. 25–47 (1976).

Dahlén, G., et al., "Putative periodontopathogens in 'diseased' and non–diseased persons exhibiting poor oral hygiene." *J. Clin. Periodontol.* 19:35 (1992).

Offenbacher, S., et al., "New clinical diagnostic strategies based on pathogenesis of disease." *Journal of Periodontal Research* 28:523 (1993).

Razmus, T.F., "Caries, Periodontal Disease, and Periapical Changes," *Dental Clinics of North America* 38(1):13 (1994).

(List continued on next page.)

*Primary Examiner*—James C. Housel
*Assistant Examiner*—Susan C. Wolski
*Attorney, Agent, or Firm*—Vincent M. Powers; Dehlinger & Associates

[57] ABSTRACT

A method of screening for the presence of a periodontal disease condition is disclosed. The method involves obtaining an oral fluid sample from a human subject being tested, and determining the level of native free pyridinium crosslinks (free pyridinoline and/or free deoxypyridinoline) from the subject. An above-normal level of crosslinks, when compared with a predetermined level characteristic of normal subjects, is an indication of the presence of a periodontal disease condition.

20 Claims, 1 Drawing Sheet

OTHER PUBLICATIONS

Talonpoika, J.T., and Hämäläinen M.M., "Collagen I carboxyterminal propeptide in human gingival crevicular fluid before and after periodontal treatment," *Scandinavian Journal of Dental Research* 101:154 (1993).

Williams, R.C., and Howell, T.H., "New technologies for the diagnosis of periodontal disease," *The Journal of Prosthetic Dentistry* 69:551 (1993).

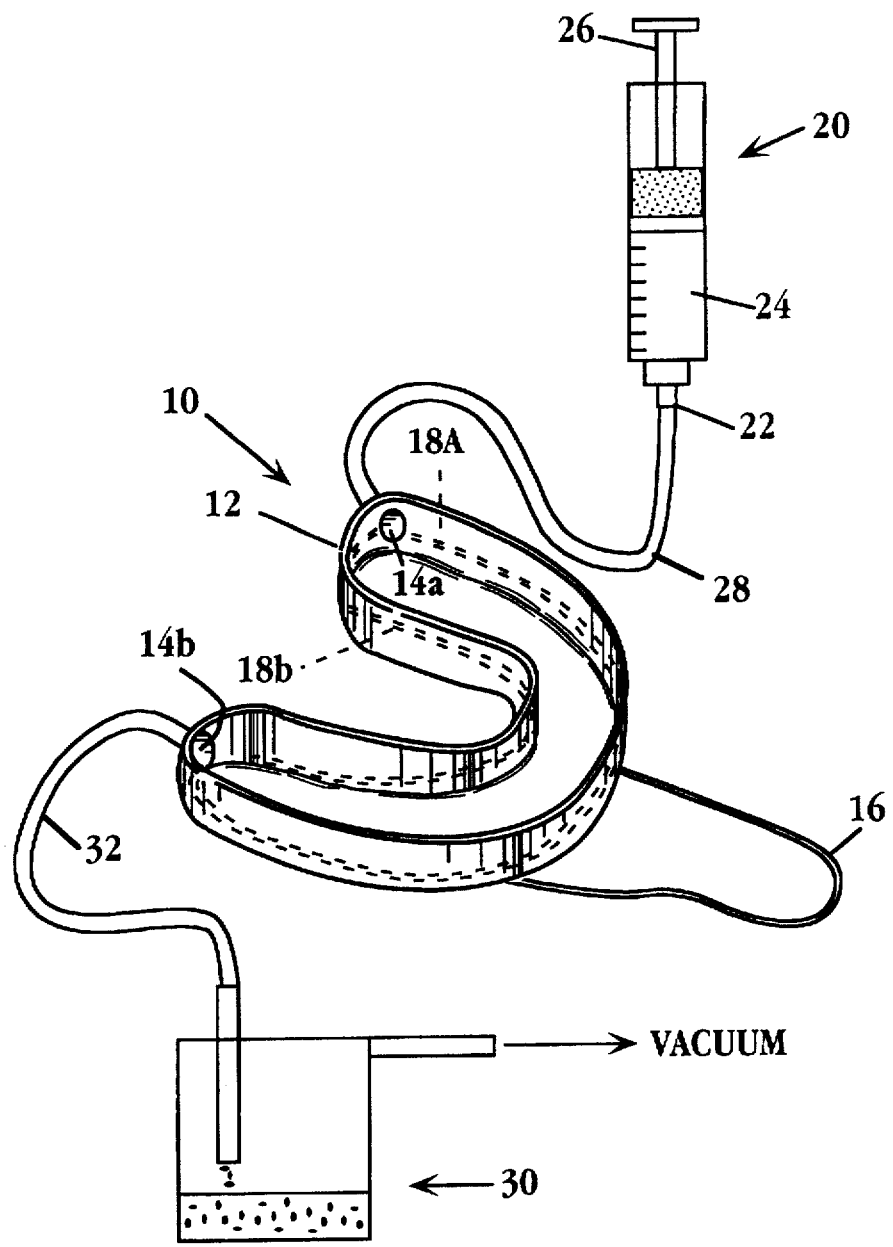

SCREENING METHOD FOR PERIODONTAL DISEASE

This application is a continuation-in-part of Ser. No. 08/209,924 filed Mar. 11, 1994, abandoned, Ser. No. 08/140,284 filed Oct. 20, 1993, abandoned, Ser. No. 07/992,936 filed Dec. 17, 1992, abandoned, and PCT Application No. PCT/US93/12321 filed Dec. 17, 1993, abandoned, all of which are incorporated herein by reference.

FIELD OF THE INVENTION

The present invention relates to methods for detecting and monitoring the presence of periodontal disease in mammals.

REFERENCES

Black, D., et al., *Anal. Biochem.* 169:197–203 (1988).

Campbell, A., *Monoclonal Antibody and Immunosensor Technology*, Elsevier (1991).

Cerelli, M. J., et al., PCT Publication No. WO 94/03814 (App. No. PCT/US93/07203) (1994).

Colwell, A., et al., in *Current Research in Osteoporosis and Bone Mineral Measurement*, Vol. 2, F. Ring, Editor, British Institute of Radiology, London, p. 5 (1992).

Dahlen, G., et al., *J. Clin. Periodontol.* 19:35 (1992).

Eyre, D. R., et al., *Anal. Biochem.* 137:380–388 (1984).

Hall, W. B., *Decision Making in Periodontology*, 2nd Ed., Mosby-Year Book, Inc., St. Louis, Mo. (1993).

Harlow, E., et al., *Antibodies: A Laboratory Manual*, Cold Spring Harbor Lab (1988).

James, I., et al., *J. Chromatogr.* 612:41–48 (1993).

James, I., et al., *Clin. Rheumatol.* 10:457 (1991).

Kieser, J. B., *Periodontics: A Practical Approach*, Wright Publishing, London, England (1990).

Kung, V. et al., PCT Publication No. WO 94/14072 (App. No. PCT/US93/12321) (1994).

Loesche, W. J., et al., *J. Periodontol.* 61:189 (1990).

Malamud, D., et al., Eds., *Saliva as a Diagnostic Fluid*, Annals New York Acad Sci., Vol. 694 (1993).

Manson, J. D., and Eley, B. M. *Outline of Periodontics*, 2nd Ed., Wright Publishing, London, England (1989).

Offenbacher, S., et al., *J. Periodontal Res.* 28:523 (1993).

Pratt, D. A., et al., *Anal. Biochem.* 207:168–175 (1992).

Razmus, T. F., *Dental Clinics of North America, The Clinical Approach to Radiologic Diagnosis*, 38:13–31 (1994).

Robins, S. P., PCT Publication No. WO 91/10141 (App. No. PCT/GB90/02030) (1991).

Segel, I., *Biochemical Calculations*, John Wiley and Sons, (1976).

Seibel, et al., *J. Rheumatol.* 16:964–970 (1989).

Seymour, R. A., and Heasman, P. A., *Drugs, Diseases, and the Periodontium*, Oxford University Press, New York (1992).

Williams, R. C., and Howell, T. H., *J. Prosth. Dent.* 69:552 (1993).

Wong, S. S., *Chemistry of Protein Conjugation and Cross-Linking*, CRC Press, Boca Raton, Florida (1991).

BACKGROUND OF THE INVENTION

Periodontal diseases comprise a variety of conditions associated with the deterioration and breakdown of the gingival and periodontal tissues surrounding the teeth. In general, the affected tissues include the alveolar bone, which forms a cavity in which the tooth resides; the periodontal ligament, a fibrous tissue which covers the alveolar bone; the cementum, a mineralized connective material joining the periodontal ligament to the root surface; and various gingival tissues (the gingival connective tissue, the gingival epithelium, and the free gingiva), which line the gum exterior and provide a bridging element between adjacent teeth (Kieser, 1990; Seymour et al., 1992).

Periodontal diseases are typically classified as either gingivitis or periodontitis, depending on the localization of tissue inflammation and breakdown. Where inflammation and tissue breakdown are confined primarily to gingival tissues, the condition is classified as gingivitis. In more advanced conditions, where degradation has progressed to tissues between the root and the alveolar bone, the condition is classified as periodontitis. Both inflammatory response elements and microbial infection are believed to contribute significantly to the progression and severity of these diseases.

Although the causes of periodontal diseases are not well understood, epidemiological studies have shown that periodontal diseases occur with greater frequency and severity among the poor, and in population subgroups who appear to be predisposed to disease onset. Without proper medical intervention, periodontal conditions can lead to pronounced inflammation of periodontal tissues, and in extreme cases, the loss of teeth.

Various methods have been proposed for detecting and/or assessing periodontal diseases. Traditional methods have been based on visual inspection of tissues to identify affected areas (Williams et al., 1993). Inflammation has been assessed based on redness, swelling, and bleeding caused by probing. Periodontal attachment loss has been assessed based on periodontal pocket depths. Although such visual techniques are intended to assess the physical state of tissues, the more modern view is that they provide only a retrospective assessment, given that considerable time may pass before metabolic changes are reflected in tissue morphology.

Radiographic techniques have been employed for assessing alveolar bone loss, but the value of these techniques has been limited by low sensitivity. The earliest signs of bone destruction are not visible radiographically until the bone has been demineralized by 40–60% (Razmus, 1994), and monitoring further changes has been difficult. Further, although subtractive radiography methods may lead to improved sensitivity in monitoring bone loss (Williams et al., 1993), such measurements are retrospective in nature and are inadequate for detecting early stages of periodontal disease.

A number of putative periodontal pathogens, such as *Bacteroides gingivalis*, *Bacteroides intermedius*, and *Actinobacillus actinomycetemcomitans*, have been proposed as markers for detection or confirmation of periodontal diseases (Loesche, 1990). It has been difficult, however, to localize the sites of infection without resorting to painstaking sample collection at multiple putative sites. More significantly, questions have been raised about the utility of such detection in view of the fact that many pathogens appear to be present in normal oral flora (e.g., Dahlen et al., 1992). For similar reasons, the measurement of pathogen-specific antibodies in serum has met with limited success since it is unclear whether elevated antibody levels reflect active periodontal destruction, or merely humoral protection resulting from a previous periodontal disease condition (Williams, 1993).

A variety of components in gingival crevicular fluid (GCF) have been studied as possible markers of periodontal diseases (Williams, 1993; Offenbacher, 1993). These components have been divided by one reviewer into classes comprising (i) products of host cells, such as lysozyme, acid and alkaline phosphatases, and glycosidases; products of host immunity, such as antibodies and interleukins; products of tissue of breakdown, such as collagens, proteoglycans, and aspartate aminotransferase; and products of microbial plaque, such as endotoxin and various enzymes (Williams, 1993). Because clinical studies on many of these components have begun only recently, their utilities with regard to periodontal disease diagnosis have not been established.

In view of the limited methods available heretofore, there is a need to develop markers useful for detecting tissue degradation associated with periodontal diseases. Ideally, such a marker should derive from periodontal tissue itself, providing a sensitive and real-time measure of the level of tissue damage taking place. In addition, the marker should have a well defined chemical structure that is measurable by immunological or other conventional analytical techniques.

SUMMARY OF THE INVENTION

The invention includes, in one aspect, a method of screening for the presence of a periodontal disease condition in a human subject. The method includes obtaining an oral fluid sample, preferably whole saliva, from the subject, and determining the level of native free pyridinoline (Pyd) and/or deoxypyridinoline (Dpd) in the sample. The determined level is then compared with a predetermined level characteristic of normal subjects, and an above-normal level is an indication that the subject has a periodontal disease condition. In one preferred embodiment, the sample level is measured by immunoassay using monoclonal or polyclonal antibodies specific for the selected crosslinks.

The method may also be used to monitor a change in the status of periodontal disease condition in the subject, in response to a therapeutic treatment, by further monitoring the level of Pyd and/or Dpd in oral fluid samples from the subject during or following such treatment.

In another embodiment, the method may further include the steps of (i) obtaining a salivary ductal sample from the subject, (ii) determining the level of such selected crosslinks in the ductal sample, and (iii) comparing the determined ductal level with a predetermined ductal level characteristic of normal subjects, where an above-normal ductal level is an indication that the subject has a bone resorption condition rather than a periodontal disease condition.

In another aspect, the invention includes a method of screening for the presence of a bone resorption condition in a human subject. The method includes obtaining a salivary ductal sample from the subject, determining a level of pyridinium crosslinks selected from the crosslink group described above, and comparing the level determined with a predetermined level characteristic of normal subjects. An above-normal ductal level is an indication that the subject has a bone resorption condition.

In one embodiment, the bone resorption condition being screened for is osteoporosis, osteoarthritis, primary hyperparathyroidism, or a bone metastasis. These and other objects and features of the invention will become more fully apparent in view of the following detailed description of the invention.

BRIEF DESCRIPTION OF THE DRAWINGS

FIG. 1 shows a tray device and assembly for collecting gingival crevicular fluid in accordance with the invention.

DETAILED DESCRIPTION OF THE INVENTION

I. Definitions

As used herein, the terms below have the following definitions:

"Pyd" or "pyridinoline" or "free pyridinoline" refers to the compound shown at I below, where the pyridinium ring nitrogen derives from the ε amino group of a hydroxylysyl residue.

"Dpd" or "deoxypyridinoline" or "free deoxypyridinoline" refers to the compound shown at II below, where the pyridinium ring nitrogen derives from the ε amino group of a lysyl residue.

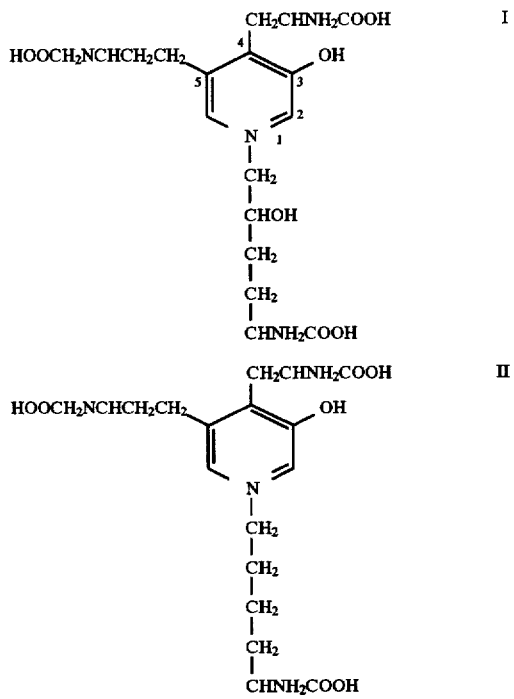

"Free crosslinks" refers to compound I, compound II, or both, i.e., pyridinoline and/or deoxypyridinoline crosslink species free from covalently attached amino acids, peptides, and glycosyl groups.

"Glycosylated pyridinoline" or "glyco-Pyd" refers to glycosylated forms of compound I, wherein glycosyl groups are covalently bound to the aliphatic hydroxyl group. Two exemplary glyco-Pyd compounds are Gal-Pyd and Glc.Gal-Pyd, which contain the acetal groups shown at III and IV below, respectively.

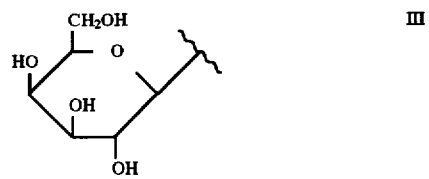

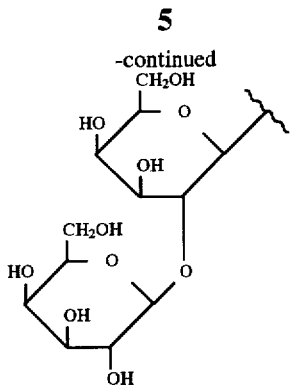

"Pyd-peptides" refers to peptide-derivatized forms of compound I, in which one or more of the three amino acid residues in the compound are linked by peptide linkages to additional amino acid residues. Similarly, "Dpd-peptides" refers to peptide-derivatized forms of compound II, in which one or more of the three amino acid residues in the compound are linked via peptide linkages to additional amino acid residues. "Pyridinium-peptides" refers to a mixture of Pyd-peptides and Dpd-peptides.

"Pyd-peptides having a molecular weight greater than 1000 daltons" or "Pyd-peptides (MW>1000)" refers to Pyd-peptides retained by a dialysis membrane having a 1,000 molecular weight cutoff. Similarly, "Dpd-peptides having a molecular weight greater than 1000 daltons" or "Dpd-peptides (MW>1000)" refers to Dpd-peptides retained by a dialysis membrane having a 1,000 molecular weight cutoff.

"Pyd crosslinks" refers to pyridinium compounds which contain compound I either in free or peptide-derivatized form. Pyd crosslinks include Pyd, glyco-Pyd and Pyd-peptides. Similarly, "Dpd crosslinks" refers to the pyridinium crosslinks which contain compound II either in free or peptide-derivatized form. "Dpd crosslinks" include Dpd and Dpd-peptides.

"Pyridinium crosslinks" refers to pyridinium crosslinks which contain compounds I and/or II in free and/or peptide-linked form.

"Native free" or "native, peptide-free" refers to a compound having structure I or II (or both) shown above, and which has not been subjected to hydrolytic conditions.

"Total Pyd" or "T-Pyd" refers to the total quantity of Pyd crosslinks present, as measurable by acid hydrolysis of a sample to completely convert Pyd crosslinks to free Pyd. Similarly, "total Dpd" or "T-Dpd" refers to the total quantity of Dpd crosslinks present.

"Hydrolysed-Pyd" of "H-Pyd" refers to Pyd produced by hydrolyzing Pyd crosslinks in 6N HCl at 110° C. for 16 hours. Similarly, "hydrolysed-Dpd" of "H-Dpd" refers to Dpd produced by hydrolysing Dpd crosslinks in 6N HCl at 110° C. for 16 hours.

As used herein, "mammal" has its standard meaning. Examples of mammals relevant to the present application include humans, dogs, cats, horses, cows, sheep, pigs, rabbits, rats, and mice.

"Periodontal disease condition" refers to an above-normal rate of collagen degradation associated with the periodontium, which may include collagen degradation in the gingiva, the periodontal ligament, the cementum, and the alveolar bone. Periodontal disease conditions include gingivitis, chronic inflammatory periodontal disease, prepubertal periodontitis, juvenile periodontitis, and rapidly progressive periodontitis.

"Bone resorption condition" refers to a condition characterized by an elevated level of bone degradation (resorption) in a mammalian subject. Bone resorption conditions include osteoporosis, osteoarthritis, rheumatoid arthritis, primary hyperparathyroidism, hyperthyroidism, Paget's disease, bone cancers (e.g., metastases in bone), osteomalacia, rickets, renal osteodystrophy, and drug-induced osteopenia.

II. Free Crosslink Detection

The present invention is based on a correlation between increased bone collagen degradation and the levels of native, peptide-free pyridinoline (N-Pyd) and deoxypyridinoline (N-Dpd) in certain oral fluids. These markers are useful in screening for the presence of bone degradation conditions, particularly periodontal disease conditions, and for monitoring the progress of therapeutic treatment of such conditions. Because these pyridinium compounds originate directly from affected collagenous tissues, they provide a current and sensitive measure of the status of bone collagen degradation. Furthermore, the screening method can provide an early warning of elevated collagen degradation, leading to early diagnosis of disease and initiation or modification of therapy as necessary.

In practicing the invention, the levels of the free pyridinium crosslinks, N-Pyd and/or N-Dpd, are measured by any analytical method capable of quantitatively measuring these compounds without significant interference from other components in the oral fluid. For this purpose, suitable methods may include chromatographic, electrophoretic, and immunoassay methods, and combinations thereof.

Processing of the oral fluid sample may include a pretreatment step to remove a substantial portion of the proteins ordinarily present in oral fluid. For example, proteins may be removed by precipitation with trichloroacetic acid, where the sample is mixed 10:1 with 50% trichloroacetic acid and then centrifuged to remove a precipitate. Alternatively, the sample may be passed through a protein A column or contacted with *Staphylococcus aureus* cells (e.g., "PANSORBIN" cells, available from Calbiochem, San Diego, Calif.) to remove immunoglobulins and the like. In another approach, the sample is filtered to remove sample components having molecular weights greater than a certain threshold, e.g., 30 kilodaltons. Such filtration may be accomplished by centrifugation using a spin filtration device or the like (e.g., a "CENTRICON"-30 device, available from Amicon, Mass.).

Where the free pyridinium crosslinks are measured by non-immunological methods, the crosslinks can be measured by fluorescence detection based on their intrinsic fluorescence properties. N-Pyd and N-Dpd strongly fluoresce with peak emission at 390–400 nm when subjected to an excitation source at about 297 nm (Black et al., 1988; Eyre et al., 1984). Chromatographic (James et al., 1993) and capillary electrophoresis (James et al., 1991) techniques for fluorimetrically measuring Pyd and Dpd have been described. Alternatively, the crosslinks may be measured based on UV-absorbance properties as described by Colwell et al. (1992).

In view of the relatively low concentrations of free crosslinks present in oral fluids, it may be desirable to concentrate the crosslinks by solvent evaporation following a purification step prior to crosslink quantitation. For example, chromatography of the oral fluid sample through CF1 cellulose is effective to remove proteins and other materials from the sample (e.g., Black et al., 1988; Pratt et al., 1992), while providing the purified crosslinks in an aqueous layer that can be removed under reduced pressure. The resultant crosslink solid is resuspended in a smaller volume than before to provide a crosslink concentration higher than that in the original sample. Similarly, reversed phase C-18 chromatography of a crosslink sample is effective to provide purified crosslinks as a Pyd-Dpd mixture in an aqueous acetonitrile mixture that is easily removed by evaporation. After suspension in a small solvent volume, the crosslinks may be processed further for quantitation of crosslinks.

N-Pyd and N-Dpd may also be measured by immunoassay techniques employing antibodies specific for N-Pyd, N-Dpd, or both. The antibodies may be monoclonal or polyclonal, as described further below. With regard to specificity, the antibodies should be sufficiently specific for the selected crosslinks (N-Pyd and/or N-Dpd) to avoid spurious results due to binding with other saliva components.

Screening and selection for such antibodies may be based on affinity for N-Pyd or N-Dpd alone, where an antibody showing an affinity for N-Pyd and/or N-Dpd of greater than about $10^7$/molar, preferably greater than about $10^8$/molar, is usually specific enough for the purposes of the invention. Binding affinity can be determined by known methods, e.g., by Scatchard analysis using an ELISA assay (Campbell, Segel). Accordingly, in one embodiment, the antibody reagent used in the invention has a binding affinity constant for the selected free crosslink species of greater than about $1 \times 10^7$/molar, and preferably greater than about $1 \times 10^8$/molar.

In addition, the screening process may be based on additional binding criteria, such as low affinities for amino acids, polypeptides, and/or other oral fluid components. For this purpose, it is convenient to measure the binding affinities of the antibodies with respect to certain pyridinium peptide forms that are obtainable from urine. Methods for obtaining such pyridinium peptide forms are described in Example 1 below. These peptides, which can be categorized by molecular weight (e.g., >1000 MW), consist of pyridinoline and deoxypyridinoline species that include peptides covalently attached to one or more amino and/or carboxyl groups of the pyridinium moiety. A high affinity for the selected free crosslinks (N-Pyd and/or N-Dpd) in combination with a relatively low affinity for N-Pyd or N-Dpd peptide forms (e.g., a binding affinity ratio of less than about 5:1 for free:peptide forms) is thus one additional criterion that can be used in the screening process. Accordingly, in one general embodiment, the antibodies have a ratio of reactivity toward the selected native free pyridinium crosslink and urinary pyridinium peptides larger than 1,000 daltons in molecular weight, of greater than about 5:1.

As another binding criterion, the antibodies can be tested for cross-reactivity with free amino acids. For this purpose, an amino acid mixture comprising all 20 standard amino acids at selected concentrations can be used, such as the amino acid mixture employed in Example 8 below.

The antibodies for use in the invention may be specific for N-Pyd, N-Dpd, or both, including antibodies which are specific for one and have moderate crossreactivity (e.g., 40%) with the other. In a more specific embodiment, where the antibody is highly specific for N-Pyd, the antibody preferably has a ratio of reactivity toward native free pyridinoline and native free deoxypyridinoline of greater than about 5:1, preferably greater than about 20:1, and more preferably greater than about 100:1. Where the antibody is for binding N-Dpd, the antibody preferably has a ratio of reactivity toward native free deoxypyridinoline and native free pyridinoline of greater than about 5:1, preferably greater than about 25:1, and more preferably greater than about 100:1. Where the antibody is for binding both native free pyridinoline and native free deoxypyridinoline, the antibody preferably has a ratio of reactivity toward native free pyridinoline and native free deoxypyridinoline of between about 2:1 and 1:2.

Example 8 illustrates a competitive binding assay for determining the relative specificities of an antibody for N-Pyd, N-Dpd, and other test materials. Briefly, purified N-Pyd, N-Dpd, urinary pyridinium crosslinks >1000 MW, and an amino acid mixture containing the 20 common amino acids in equimolar amounts (150 μM each), are reacted with a limiting amount of a crosslink-specific antibody in the presence of a selected free crosslink (e.g., N-Pyd, when seeking N-Pyd-specific antibodies) immobilized on a solid-support under conditions where the test materials compete with the support-bound crosslink for binding to the antibody. The extent of binding of antibody to the support-immobilized crosslinks provides a measure of the relative reactivities of the test materials for the antibody.

The adequacy of binding specificity for selected antibodies may be verified using a complementary measurement technique (e.g., capillary electrophoresis or C-18 reversed phase HPLC), or by spike-recovery experiments, where known amounts of N-Pyd or N-Dpd are added to oral fluid samples and the resultant measured levels are compared with predictions based on the level of N-Pyd or N-Dpd measured in the original sample.

The immunogen for producing the antibody reagent is Dpd or Pyd conjugated to a carrier molecule, typically a carrier protein such as keyhole limpet hemocyanin (KLH) or a mammalian serum albumin. The Pyd and Dpd can be native, hydrolyzed, or synthetic. Methods for obtaining N-Pyd and N-Dpd are known (Black et al., 1988; Seibel et al., 1989; Robins, 1991; and Cerelli et al., 1994), with a particular method provided in Example 1. Similarly, hydrolyzed Pyd or Dpd can be produced by acid hydrolysis of pyridinium crosslinks in bone collagen or urine, as described in Black et al. (1988) and Seibel et al. (1989).

In another approach, the Pyd and Dpd are prepared synthetically, as described, for example, in EPO Publication No. 556152 A1 (Revesz, 1993).

Coupling of Pyd or Dpd to a carrier protein is by standard coupling methods, typically using a bifunctional coupling agent which forms, at one coupling end, an amide linkage with one of the free carboxyl (or amino) groups of Pyd or Dpd, and at the other coupling end, an amide or ester or disulfide linkage to the carrier protein according to standard methods. Alternatively, in a preferred embodiment, the Pyd or Dpd can be directly coupled to the protein, e.g., in the presence of a water-soluble carboxyl activating agent such as EDC (1-(3-dimethylaminopropyl)-3-ethylcarbodiimide), also according to well known methods. The latter approach is illustrated in Examples 2A and 2B, which describe the coupling of Pyd to bovine serum albumin (BSA) and keyhole limpet hemocyanin (KLH) by EDC activation. General coupling reactions for derivatizing a carrier protein with a peptide antigen are given in Harlow (1988, pp. 77–87) and Wong (1991).

For preparing monoclonal antibodies, an immunogen of the type above is used to immunize an animal, such as a mouse, from which antigen-specific lymphocytes can be obtained for immortalization. One suitable animal is the "autoimmune" MRL/MpJ-lpr mouse available from Jackson Laboratory (Bar Harbor, Me.).

Where an antibody specific for N-Pyd is desired, a Pyd-immunogen is typically used. Likewise, where an antibody which is specific for N-Dpd is desired, a Dpd-immunogen is typically used. An antibody which recognizes both Pyd and Dpd may be obtained using a Pyd-immunogen or a Dpd-immunogen.

To produce the desired antibodies, the hybridoma cell line is grown in a suitable medium (Harlow, pp. 247–270), such as Dulbecco's modified Eagle's medium (DMEM) supplemented as described in the Materials and Methods section below. Monoclonal antibodies ("Mabs") are harvested from the medium and can be concentrated and stored according to published methods (Harlow pp. 271–318). An exemplary protocol for preparing monoclonal antibodies having the desired specificity is provided in Example 3. The properties of monoclonal antibodies specific for N-Pyd, N-Dpd, and both N-Pyd and N-Dpd, are shown in Tables 4–6 in Example 3.

Polyclonal antibody preparation is by conventional techniques, including injection of the immunogen into suitable mammalian subjects, such as rabbits, sheep or mice, according to immunological protocols generally known in the art (e.g., Harlow, pp. 93–115). Typically, rabbits are injected subcutaneously with the immunogen in an adjuvant, and booster immunizations are given by subcutaneous or intramuscular injection every 2–3 weeks; mice may be injected intraperitoneally according to a similar schedule. Blood is collected at intervals, e.g. 1–2 weeks after each immunization injection. Antisera may be titrated to determine antibody formation with respect to N-Pyd or N-Dpd, according to standard immunoprecipitation methods (Harlow, pp. 423–470). Details of one method for producing polyclonal antibodies in rabbits are given in Example 4.

The binding affinity for polyclonal antisera can be determined by known methods and represents an average binding affinity constant for the antibodies in the antisera which are specific against the selected free crosslinks. Polyclonal antibodies obtained from rabbit VI-8 (Example 4) were found to have a binding constant for N-Pyd of about $1 \times 10^8$, as determined by Scatchard analysis. Other binding properties of the polyclonal antibodies from rabbit VI-8 are shown in Table 9.

For clinical use, crosslink-specific antibodies of the type above may be formulated in a diagnostic kit. The kit includes an antibody of the type described above, and any other suitable reagents for carrying out the assay. The assay format may be heterogeneous or homogeneous.

The immunoassay kit may take the form of a competitive assay, in which a selected amount of free crosslinks is immobilized on a solid support, for competing with free crosslinks from the sample for binding to crosslink-specific antibodies. Conveniently, the assay includes reporter-labeled second antibodies for binding to the crosslink-specific antibodies, allowing the amount of crosslink-specific antibody bound to the solid support to be determined. The label can be a radioisotope, a fluorescent or chemiluminescent label, or an enzyme, for example. Reporter-labeled second antibodies are commercially available or are readily constructed (Harlow, pp. 319–358) for a variety of reporter moieties. One preferred reporter is alkaline phosphatase, which can react with a p-nitrophenylphosphate substrate to produce a colored product having a strong absorption peak at 405 nm. An exemplary immunoassay protocol is provided in Example 6 below.

The reporter-labeled second antibody is typically an anti-IgG antibody, such as an anti-rabbit-IgG antibody, where the crosslink-specific antibodies are polyclonal antibodies obtained from immunized rabbits, or an antimouse-IgG antibody, where the crosslink-specific antibodies are mouse monoclonal antibodies. It will be appreciated that various other detection modes may be employed, such as a biotin-labeled second antibody in combination with a reporter-labeled streptavidin.

Alternatively, the crosslink-specific antibody itself can be labeled with a reporter.

In another competitive format, the crosslink-specific antibodies are immobilized on a solid support, and crosslinks from the sample compete with reporter-labeled free crosslinks for binding to the immobilized antibody. The antibodies may be attached to the solid support by a variety of known methods, including chemical derivatization or high-affinity binding of the antibody by support-bound protein A or anti-IgG antibody, according to standard methods. Reporter-labeled free crosslinks can be prepared by standard methods as well, by covalent attachment of the selected label to the amino or carboxyl groups present in the free crosslinks, for example. A detailed example of this type of assay format for measuring N-Pyd or N-Dpd is described in PCT Publication No. 94/14072 (Kung et al.).

It will be appreciated that a number of other immunoassay techniques may be used, such as radioimmunoassays, coupled enzyme assays, fluorescence-based assays, chemiluminescence assays, and EMIT-type assays.

III. Assay Method

The present invention includes, in one aspect, a method of screening for the presence of a periodontal disease condition in a mammalian subject, particularly a human subject. In the method, an oral fluid sample is obtained from the subject, and the level of selected pyridinium crosslinks, that is, of N-Pyd, N-Dpd, or a combination thereof, is determined in the sample. The measured level is compared with the level characteristic of normal subjects, and an above-normal level is an indication that the subject has a periodontal disease condition.

The oral fluid tested is a gingival crevicular fluid sample, or more conveniently, a whole saliva sample. The term "gingival crevicular fluid" refers to the fluid exudate which seeps from the gingival crevices and into the oral cavity. "Whole saliva" refers to the mixture of glandular saliva and gingival crevicular fluid ordinarily present in the oral cavity under resting state conditions. Although gingival crevicular fluid is the principal source of the N-Pyd and N-Dpd released due to periodontal disease, the applicants have found that whole saliva may be used as the test sample, apparently because the levels of N-Pyd and N-Dpd released into the crevicular fluid are greater than those in normal whole saliva. Thus, resting state whole saliva serves as a collection vehicle for the crevicular fluid.

The samples may be collected by conventional means. Where the sample is human whole saliva, the subject is asked to expectorate into a collection vial. Sample collection is preferably conducted in a relaxed environment to avoid sudden development of dry mouth which would otherwise impede sample collection. It is also preferred that efforts not be made to stimulate or over-stimulate salivation in the subject, as excess salivation can potentially dilute the levels of N-Pyd and N-Dpd originating from the gingival crevicular fluid.

In another approach, whole saliva is collected using an absorbent pad which is placed between the lower cheek and gums of the subject. The pad comprises any pharmaceutically acceptable material, such as cotton or a cellulose material, that does not significantly bind N-Pyd or N-Dpd. To minimize such binding, the pad may be pretreated with salts and/or blocking agents such as are disclosed in U.S. Pat. No. 5,103,836 (Goldstein et al., 1993). Typically 0.2 to 2 ml of saliva is collected over the course of a few minutes.

After the sample has been collected, the pad is removed from the subject's mouth and is compressed or centrifuged to release the fluid from the pad into a storage container or test device. Suitable devices for collecting oral fluid include the pad-compression device disclosed in U.S. Pat. Nos.

4,418,702 and 4,580,577, the pad-syringe devices disclosed in PCT Pub. No. WO 94/04078 (Thieme et al., 1994; which corresponds to U.S. Pat. No. 5,339,829) and EP Pub. No. 520,408 A2 (Seymour, 1992; which corresponds to U.S. Pat. No. 5,260,031); and the absorbent pad-centrifuge devices described in PCT Pub. No. WO 91/13355 (Goldstein et al., 1991) and U.S. Pat. No. 4,774,962 (Hebel et al., 1988). The collected sample may be stored for transport to a clinical testing site for analysis using methods discussed in section II above.

Where the test sample is gingival crevicular fluid, the sample may be collected by dabbing multiple gingival crevice sites with a small absorbent pad such as described above (e.g., with a pad volume of 50–200 μL), preferably until the pad is saturated, and then expressing or centrifuging the contents of the pad into a container for storage or immediate testing. Collection using traditional paper points is less suitable due to the low sample volumes collected and the possible contamination of the sample with blood from tissue inflammation at some sites.

Alternatively, a snugly fitting tray device may be placed around the subject's upper dentition (teeth and gums), such that a rinse solution is used to wash gingival crevicular fluid into the tray. The collected washings are then transferred to a storage container by aspiration or other suitable means.

An exemplary tray device for use in the method is shown at 10 in FIG. 1. Device 10 includes a tray element 12, inlet and outlet ports 14a and 14b for admitting rinse solution, and optionally a removal means 16 (e.g., a string or plastic wire) for removing the device from the subject's mouth. Tray element 12 is made of a soft, pliable polymer material (e.g., standard rubber or plastic materials used in the medical arts) for fitting comfortably around the dentition and gum tissue of the subject's upper or lower jaw. The dimensions of the tray element are selected so as to create an air-tight seal with the teeth and gingiva when a vacuum is applied through port 14a or 14b, ensuring the presence of only gingival crevicular fluid within the tray element.

Tray element 12 may also include a plurality of channels 18a and 18b which run along the entire length of the tray element (along the anterior and/or posterior faces of the dentition), for directing rinse solution across the gingival tissues. Preferably, such channels are situated within the walls of the tray device to direct rinse solution over or in close proximity to the junctional epithelia, where the gingiva attach to the teeth.

In operation, device 10 is used in combination with a reservoir for supplying rinse solution to the tray element, and a collection device 30 in which the washings are to be collected. In FIG. 1, the reservoir is a syringe 20 whose outlet 22 is in liquid communication with port 14a via tubing means 28, and the collection device is a suction filter device 30 in liquid communication with port 14b via tubing means 32.

For collecting a gingival crevicular fluid sample, syringe 20 is filled with a selected volume of rinse solution 24 (e.g., 1 to 5 mL) and then connected to inlet 14a using tubing means 26. Similarly, filter device 30 is connected to outlet port 14b using tubing means 32. Tray element 12 is then fitted snugly over the subject's dentition and gums (upper or lower jaw), and a vacuum is applied to filter device 30 such that the walls of tray element 12 press against and form a tight seal with the enclosed teeth and gum tissue. At this stage, the tray element may be inspected and adjusted to ensure a snug and uniform fit.

After a good fit has been established, rinse solution 24 is introduced into the tray element by depression of plunger 26, so that the solution enters the tray device via port 14a and passes over the gingiva. Because of the vacuum applied to the assembly, the gingival washings exit tray element 12 via port 14b and collect at the bottom of suction filter device 30. Upon completion of this washing step, the vacuum is released, the tray element is removed from the subject's mouth, and the collected sample is transferred to a storage container for testing.

Many variations of the FIG. 1 device are also possible in accordance with the invention. In particular, the tray device may be configured to cover selected subgroups of teeth. With many non-human mammals in particular, the teeth are arranged in groups separated by sizeable gaps, rather than being contiguous as in normal humans. Thus, for veterinary testing of sheep and dogs, for example, the tray device may be adapted to fit over the incisors exclusively. Of course, a tray having limited tooth coverage may also be useful in humans.

In practicing the screening method of the invention, it is necessary to ascertain an average level or range of the selected free crosslinks which is characteristic of normal subjects, against which the levels measured in the test subjects are to be compared. Accordingly, free crosslink levels are measured in oral fluid samples from a control group of subjects who are in good health and show healthy periodontal tissues, as judged by visual inspection of gum tissues and/or conventional probing techniques. The makeup of the control group may be tailored according to the characteristics of the population to be tested. For example, the control group may be limited to a particular age group, e.g. subjects 60–70 years of age, for obtaining baseline levels characteristic of the elderly. Other parameters of interest may include the subjects' weight, race, or gender, for example. The determined average or range of free crosslinks in the normal subjects is then used as a benchmark for detecting above-normal levels indicative of a periodontal disease condition.

Table 1 shows the levels of salivary N-Pyd measured in various subjects with periodontal conditions ranging from excellent to seriously diseased. The apparent periodontal condition of each individual was determined using the Periodontal Screening and Recording (PSR) Index established by the World Health Organization (WHO) (Table 1).

TABLE 1

| PSR | Periodontal Pocket Depth (mm) | Inflammation | Description |
| --- | --- | --- | --- |
| 1 | 0–3.5 | – | healthy |
| 2 | 0–3.5 | + | gingivitis |
| 3 | 3.5–5.5 | + | incipient periodontitis |
| 4 | >5.5 | + | periodontitis |

For each individual, three sextants (two lateral and one anterior) were scored for each jaw (total of six sextants), with the canine teeth defining the boundaries of the anterior sextants. Pocket depths were measured using a balled-tip probe, and for each sextant, a maximum score was recorded. After the assessments were complete, saliva samples were collected from the subjects and stored at −20° C. for later measurements of N-Pyd by the protocol described in Example 6. The results are shown in Table 2.

TABLE 2

| Sample | Age, Gender | Description | PSR | Pyd (nM) |
|---|---|---|---|---|
| LM-01 | 30, f | excellent gingival health | 1 | 0.23 |
| SFM | 48, m | 1 or 2 #3-type pockets | 3 | 0.53 |
| DH-01 | 45, f | missing teeth, recession | 2 | 0.72 |
| LK-01 | 20's, f | gingivitis | 2 | 0.84 |
| DK-01 | 39, m | active disease, recent flare-up | 3 | 1.2 |
| SMM | 38, m | #4 pockets, all sextants | 4 | 1.7 |
| SFC | 40, m | #4 pockets, all sextants, pre-treatment | 4 | 2.1 |
| SFD | 41, m | SFC patient, post treatment | 4 | 1.1 |

With reference to Table 2, test subject LM-01, who was characterized as having excellent gingival health, showed an N-Pyd level of 0.23 nM which established an approximate baseline for healthy periodontal tissue. The remaining data in Table 2 show that the levels of salivary N-Pyd measured in the other subjects correlated with the degree of gingival pocketing. For example, subject SFM, who was diagnosed as having 1 or 2 #3 pockets, showed an N-Pyd level of 0.53 nM, which was more than double the value found in healthy subject LM-01. Test subject DK-01, who showed clinical manifestations of active disease, showed an N-Pyd level of 1.2 nM. Subjects with #4 pockets in all sextants (SMM and SFC) showed high N-Pyd levels of 1.7 and 2.1 nM.

Further, the more than two-fold concentration difference between the healthy subject (LM-01) and the subject with 1 or 2 #3 pockets demonstrates the ability of the assay method to detect early stages of periodontal disease.

While the method of the invention is useful in screening subjects for the presence of a periodontal disease condition, the method also finds application in monitoring the course of a periodontal disease and the efficacy of therapeutic treatment. Accordingly, free crosslink levels can be monitored following root planing, curettage or surgery, for example, to monitor the progress of tissue healing and detect any recurrence of tissue degradation. Similarly, free crosslink monitoring can be conducted during and after antibacterial treatment (e.g., systemic treatment with tetracycline or amoxicillin/clavulanate potassium) to reduce the levels of deleterious bacteria in the oral cavity. The monitoring of other dental-related therapies is also contemplated.

An illustration of the monitoring aspect of the invention is found in the last two rows of Table 2. The second to last row shows data from a subject showing #4 type pockets in all sextants, with a measured salivary N-Pyd level of 2.1 nM prior to treatment. Following the first crosslink measurement, the subject underwent conventional scaling and root planing to try to remove the diseased tissues. Several months after treatment, the subject's N-Pyd level was determined again. As seen from the last row of Table 2, the N-Pyd level had dropped to 1.1 nM, indicating that periodontal tissue degradation had significantly diminished following treatment. Further follow-up measurements could be used to assess the progress of healing and provide a warning of recurrence of tissue degradation.

The data in Table 2 indicate that N-Pyd levels measured in whole saliva samples provide a useful indication of the degree of ongoing periodontal tissue degradation. However, it may also be desirable to measure another salivary component as a standard to assess saliva dilution. Such a standard may be used to normalize free crosslink measurements with regard to dilution caused by the subject's recent intake of a drink, or by the presence of an unrelated disease condition affecting the production of saliva in the subject. For example, total salivary protein can be used as the standard, as measured by conventional methods, i.e., by Lowry, Bradford, or BCA assay, which are well known in the art.

In another embodiment, the screening method may additionally include the steps of (i) obtaining a salivary ductal sample from the subject, (ii) determining the level of such selected crosslinks in the ductal sample, and (iii) comparing the determined ductal level with a predetermined ductal level characteristic of normal subjects.

The ductal sample can be collected from the parotid ducts, the submaxillary ducts (also known as submandibular ducts), the sublingual ducts, and other minor ducts situated inside the lips, along the palate, and at various sites along the cheeks. Methods for collecting such samples from specific duct sources are known in the art (e.g., Malamud et al., 1993). Preferably, the sample is a parotid duct sample collected by cannulation or suction, or consists of a pooled submandibular/sublingual sample collected by aspiration from the bottom of the subject's mouth.

An above-normal ductal crosslink level is an indication that the subject has a bone resorption condition rather than a periodontal disease condition. Conversely, where the ductal crosslink level is normal but crosslink level in a gingival crevicular fluid or whole saliva sample is above-normal, the subject likely has a periodontal disease condition.

In a related aspect, the invention also includes a method of screening for the presence of a bone resorption condition in a mammalian subject. The method includes obtaining a salivary ductal sample from the subject, determining the level of Pyd and/or Dpd in the sample, and comparing the level determined with a predetermined level characteristic of normal subjects, where an above-normal level is an indication that the subject has a bone resorption condition. In a preferred embodiment, the resorption condition screened for is a periodontal disease or osteoporosis.

It will be appreciated that the method is complementary to the method of screening for periodontal disease conditions discussed above. Detection of increased bone resorption that is unrelated to periodontal disease indicates that further investigation of the subject's health is warranted. Such investigation may take the form of a blood or urine assay described in PCT Publication Nos. WO 91/10141 (1991), WO 94/03814 (1994), and WO 94/14072 (1994), for measuring N-Pyd and N-Dpd as markers of bone resorption. Other conventional diagnostic procedures may also be used, such as radiographic densitometry measurements and the like.

IV. Utility

The present invention provides a method of screening for periodontal disease conditions which, in contrast to a number of previous diagnostic methods, is reflective of the real-time status of collagen tissue degradation in periodontal disease. The method provides early detection of disease conditions that might not otherwise be diagnosed because lesions have not progressed enough to be visually detected, or because the pattern of bone destruction involves more recession (of the gingiva from the enamel) than pocketing and therefore is not recognized as a form of periodontal disease. Early detection is highly desirable because gingivitis is a reversible condition which can be controlled by early therapeutic intervention, whereas periodontitis and other more serious conditions are more difficult to treat, and their bone-destructive effects are relatively irreversible.

The method also has use in veterinary applications in detecting and monitoring the treatment of periodontitis-like conditions that occur among farm animals and house pets. Conditions that produce destruction of alveolar bone are common among cats, horses and dogs, and often require veterinary treatment. In sheep, a periodontal condition known as "broken mouth" causes the loss of incisor teeth, leading to death by starvation because the sheep are no longer able to graze. This results in considerable economic loss in the sheep industry. Accordingly, the method is useful in identifying affected animals so that treatment can be initiated if appropriate.

Finally, the method may also be used with other oral diagnostic methods, such as radiographic techniques and bacterial sampling, to provide a fuller picture of the subject's status.

From the foregoing, it will be appreciated how various objects and features of the invention are met. The invention provides simple, non-invasive methods for detecting and monitoring periodontal disease conditions, and for screening for bone resorption conditions generally. The free crosslinks originate directly from the sites of degradation, providing a real-time measure of the status bone degradation and an early warning of disease onset. The free crosslinks also provide a sensitive marker for monitoring changes in disease status during or following therapeutic treatments. Further, the periodontal screening method is advantageous from the standpoint that only a single sample need be collected for screening, in contrast to established probing methods which require careful inspection of many gingival sites.

The following examples are intended to illustrate, but in no way limit the invention.

EXAMPLES

Materials and Methods

Female autoimmune MRL/MpJ-lpr mice were purchased from the Jackson Laboratory, Bar Harbor, Me.

Mouse non-secreting P3X63Ag8.653 myeloma cells, and mouse monocyte-macrophage cell lines P388D1(IL-1) and J774A.1 were purchased from American Type Culture Collection (ATCC), Rockville, Md.

Adjuvant Ribi and Ribi(CWS) were purchased from RIBI Immunochem Research, Inc., Hamilton, Mont. 50% PEG 1500 (polyethylene glycol 1500, 50% (w:v) in water) was purchased from Boehringer Mannheim, Indianapolis, Ind. HAT and HT were purchased from Sigma Chemical Company, St. Louis, Mo.

Dulbecco's Modified Eagle Medium (DMEM), NCTC-109, and gentamicin were purchased from Gibco, Grand Island, N.Y. Fetal clone bovine serum was from Hyclone Laboratories, Inc., Logan, Utah. Oxaloacetic acid and insulin were from Sigma Chemical Company. S-DMEM was formulated as follows, where the percentages indicate final volume percentages in the final medium: DMEM (80%), NCTC-109 (10%), fetal clone bovine serum (10%), oxaloacetic acid (1 mM), L-glutamine (2 mM), gentamicin (50 µg/ml) and insulin (10 µg/ml).

For preparation of conditioned media, mouse monocyte cell lines P388D1 (IL-1), or interchangeably, cell line J774A.1, were grown in S-DMEM medium, with a 1:4 split twice a week. Every 3 days, tissue culture supernatants were filtered through a 0.2 micron filter and then supplemented with 4 mM L-glutamine. The resultant concentrated conditioned media were used as 20% supplement for S-DMEM to raise hybridoma cells.

Unless stated otherwise, PBS is defined as a buffer containing 0.01M phosphate and 150 mM NaCl, pH 7.

Example 1

Purification of Crosslinks

For preparing N-Pyd, N-Dpd, and pyridinium peptide crosslinks having a molecular weight greater than 1000 daltons, human urine was filtered through a 3000 dalton molecular cut-off filter (Filton Co.) using 40 psi of back pressure. The filtrate was then lyophilized and reconstituted in 1/20 of the original volume with 0.2M acetic acid.

The concentrated urine was then applied to a Sephadex G-10 (2.6×95 cm) column equilibrated with 0.2M acetic acid. Fractions eluted from the column were analyzed for free Pyd and free Dpd by HPLC (Black et al., 1988). The free crosslink-containing fractions were pooled together, adjusted to pH 2.0 and applied onto 1×18 cm cation exchange column (Lacarte Co., UK) and equilibrated with 0.1M sodium citrate pH 4.2.

Glyco-Pyd, Pyd and Dpd were coeluted thereafter from the ion exchange column with 0.1M sodium citrate pH 4.2. Collected fractions were analyzed for the presence of crosslinks by HPLC analysis as above. Fractions containing N-Pyd and N-Dpd were pooled together and applied to 2.5×10 cm reverse phase C-18 column (Waters) which was subsequently developed with 2–20% gradient of acetonitrile containing 0.1% HFBA. Separated fractions (glyco-Pyd, Pyd and Dpd) were collected and concentrated by lyophilization. The dry residue was reconstituted in 0.2M acetic acid and stored at 4° C.

Urinary pyridinium-peptides (MW<1000 MW) were prepared by exhaustive dialysis of human urine using 1000 dalton molecular weight cut-off dialysis membranes (Spectra-Por). The T-Pyd and T-Dpd crosslink contents of the pyridinium peptides were determined by hydrolyzing peptide samples with 6N HCl at 110° C. for 16 hours followed by HPLC analysis for Pyd and Dpd.

Preparative amounts of H-Pyd and H-Dpd were obtained from hydrolyzed powdered bovine or sheep bone as described by Black et al. (1988).

Example 2

Immunogen Preparation

A. Pyd-BSA Immunogen

To a 3.1 ml solution consisting of 9 mg of bovine serum albumin (BSA) and 3.8 mg of Pyd in 0.1M MES pH 5.0 was added an 0.88 ml aqueous solution containing 88 mg of EDC. The mixture reacted for four hours at room temperature then was exhaustively dialyzed versus phosphate buffered saline pH 7.0 (PBS). UV and fluorescence measurements indicated 5.8 moles of pyridinoline substituted per mole of albumin.

B. Pyd-KLH Immunogen

To a solution of dried H-Pyd (6 mg) in water adjusted to pH 5±0.5 (200 µl) was added 2 ml of a 10 mg/ml solution of keyhole limpet hemocyanin (KLH) in PBS. To the mixture was added 30 mg solid 1-(3-dimethylaminopropyl)-3-ethylcarbodiimide (EDC, Pierce), and ten minutes later, another 30 mg of EDC, and the reaction was allowed to proceed for 4 h at room temperature. The reaction mixture was then exhaustively dialyzed versus PBS, after which the Pyd-KLH immunogen was collected and stored.

Example 3

Preparation of Anti-Pyd Monoclonal Antibodies

A. Immunization Protocol

Female 5-week-old autoimmune MRL/MpJ-lpr mice were immunized using the protocol below:

TABLE 3

Immunization Protocol for Pyd Mice

| Immuniza-tion | Days from Fusion | Immunogen Injected (μg) | [1]Adjuvant | Inject. Mode |
|---|---|---|---|---|
| 1 | 60 | 100 | Ribi | ip[2] |
| 2 | 46 | 100 | Ribi | ip |
| 3 | 32 | 100 | Ribi | ip |
| 4 | 18 | 100 | Ribi | ip |
| 5 | 4 | 200 | — | iv[3] |

[1]Adjuvant and antigen were suspended in Hank's balanced salt solution
[2]Intraperitoneal
[3]Intravenous On the day of fusion, the immunized mouse was sacrificed by $CO_2$ gas, and the spleen was excised from the mouse and placed in a culture dish containing 5 ml of serum-free DMEM medium preheated to 37° C. Following removal of adipose tissue attached to the spleen, the spleen was washed with 5 ml of serum-free DMEM medium. The spleen was then cut into small pieces which were placed in a cell homogenizer containing 7 ml of serum-free DMEM medium, and the cells were homogenized to form a cell suspension.

B. Fusion Protocol

The following steps were performed at room temperature.

The spleen cell suspension (~$2\times10^8$ cells in serum-free DMEM medium) and log-phase P3X63Ag8.653 myeloma cells (~$7\times10^7$ cells in serum-free DMEM medium) were centrifuged independently at 400 xg for 10 min. The resultant cell pellets were suspended together in serum-free DMEM medium (10 ml) in a 50 mL centrifuge tube and then centrifuged at 400 xg for 10 min. The supernatant was removed completely, and the centrifuge tube was tapped to loosen the cell pellet.

For cell fusion, a solution of 50% PEG 1500 (4 ml) was added dropwise to the tube with gentle mixing by pipette over a 90 second period. Next, serum-free DMEM (4 ml) was added dropwise over 1 min. S-DMEM (40 ml) was then added over 2 min with gentle mixing, after which the mixture was mixed by pipette for an additional 2.5 min. The resultant mixture was centrifuged at 400 xg for 10 min. After thorough removal of the supernatant, the cells were suspended in 320 ml of HAT in 20% P388D1-conditioned S-DMEM medium. The cell suspension was plated in 16 96-well tissue culture plates, 200 μl/well, and the plates were then incubated at 37° C. in an atmosphere containing 7% $CO_2$. The cell mixtures were fed at day 3 and day 7 by removing 100 μl/well of old medium and adding 150 μl/well of either HAT medium (day 3) or HT medium (day 7). The wells were ready to screen 7 to 10 days after fusion.

C. Screening Hybridomas for Production of Anti-N-Pyd Antibodies

Successful fusion products were screened for immunoreactivity using the immunoassay format described in Example 6. Cell lines which showed high affinity binding to N-Pyd were subcloned by limiting dilution and further screened for production of antibodies with high binding affinity for N-Pyd.

D. Monoclonal Antibodies Specific for N-Pyd and/or N-Dpd

The binding properties of three highly specific antibodies obtained by the procedures outlined in sections A–C above are shown in Tables 4–6. The Pyd-specific antibody shown in Table 4 (from a cell line designated as Pyd XXV-3G6-3B11-1A10) was obtained using H-Pyd-KLH immunogen prepared as in Example 2B. The Dpd-specific and Dpd/Pyd-specific antibodies shown in Tables 5 and 6, respectively (from cell lines designated as Mab-Dpd-II-7B6-1F4-1H11 and Pyd/Dpd-V-6H2-2H4-1E4), were obtained using H-Dpd-KLH, also prepared as in Example 2B.

TABLE 4

Cross-Reactivity of N-Pyd-Specific Mab

| | |
|---|---|
| N-Pyd | 100% |
| N-Dpd | 16% |
| Pyd-Peptide (>1000) | <1% |
| Amino Acid Mixture (150 μM) | <1% |

TABLE 5

Cross-Reactivity of N-Dpd-Specific Mab

| | |
|---|---|
| N-Dpd | 100% |
| N-Pyd | <1% |
| Dpd-Peptide (>1000) | 13% |
| Amino Acid Mixture (150 μM) | <1% |

TABLE 6

Cross-Reactivity of N-Pyd/N-Dpd-Specific Mab

| | |
|---|---|
| N-Dpd | 100% |
| N-Pyd | 102% |
| Dpd-Peptide (>1000) | 1% |
| Pyd-Peptide (>1000) | 11% |
| Amino Acid Mixture (150 μM) | 5% |

Example 4

Preparation of Anti-Pyd Polyclonal Antibodies

New Zealand white rabbits (a total of 59) for immunization were divided into eight groups according to immunization protocol, as indicated below in Table 7. The immunization dose was 200 μg of Pyd-BSA (Example 2A), low-hapten Pyd-BSA immunogen (prepared as in Example 2A, but with a lower Pyd:BSA stoichiometry), or Pyd-KLH (Example 2B), in 1.0 ml PBS mixed with 1.0 ml of Ribi adjuvant (Ribi ImmunoChemical Research, Inc.). Initial immunization was by subcutaneous injections at multiple sites, and subsequent booster immunizations were given at three week intervals intramuscularly. Antiserum was collected 10 days after each immunization.

TABLE 7

| Program # | # of Rabbits | # Rabbits Kept | Carrier |
|---|---|---|---|
| I | 4 | 1 | BSA |
| II | 10 | 0 | BSA |
| III | 10 | 2 | BSA |
| IV | 5 | 1 | BSA |
| V | 5 | 2 | BSA |
| VI | 10 | 1 | KLH |
| VII | 5 | 0 | Low Hapten BSA |
| VIII | 10 | 1 | BSA |
| TOTALS | 59 | 8 | |

Upon collection, each antiserum was tested for Pyd binding affinity using the assay format described in Example 6. In brief, binding of anti-Pyd antibodies to Pyd immobilized on a solid support was detected using an alkaline phosphatase-labeled goat anti-rabbit IgG antibody reagent.

Immunized animals were kept if their antisera satisfied the following cross-reactivity criteria: amino acids (AA)<20%;

Pyd-peptide<10%; titer>5000; and a 0 to 25 nM Pyd signal separation of >10% of total modulated signal.

Profiles of the most strongly reactive antisera are shown in Table 8 below, as measured using the assay format described in Example 6. The first column indicates the immunization program from which the rabbit antiserum came. The second column indicates the bleeds used for analysis, where the bleeds were characterized separately, and their measured properties averaged to provide the values shown in the table for the respective antisera. The column marked "titer" indicates the average dilution of each antiserum necessary to achieve an optical density reading of 1.2 to 1.6 with a Pyd-negative sample (no Pyd present) in the immunoassay. The column marked "AA" shows the cross-reactivity of each antiserum with the amino acid mixture described in Example 6. The column marked "Pyd-pep >1000 MW" shows the cross-reactivity of each antiserum with Pyd-peptides (>1000 MW). The last column shows the separation between signals for 0 and 25 nM Pyd samples as a fraction of the total modulated signal.

TABLE 8

| Rabbit # | Bleeds | Titer | AA | Pyd-pep. >1000 MW | Sens. 25 nM |
|---|---|---|---|---|---|
| I-3 | 21–28 | 200K[1] | 2% | 4.6% | 18% |
| III-3 | 11–18 | 20K | 16% | 8.3% | 37% |
| III-5 | 11–18 | 52K | 1% | 8.1% | 13% |
| IV-4 | 4–14 | 84K | 4% | 4.9% | 10% |
| V-3 | 4–14 | 22K | 18% | 4.0% | 15% |
| V-4 | 11–14 | 9700 | 15% | 5.2% | 29% |
| VI-8 | 2–11 | 30K | 10% | 0.6% | 61% |
| VIII-4 | 3–10 | 34K | –0% | 3.4% | 11% |

[1]K = × 1000.

As can be seen, rabbits III-3, V-4, and VI-8 showed significant modulation of signal from 0 to 25 nM N-Pyd. The binding properties of the antibodies with the highest binding activity (VI-8) are shown in Table 9.

TABLE 9

| Cross Reactivity of N-Pyd Polyclonal Antibody | |
|---|---|
| N-Pyd | 100% |
| N-Dpd | <10% |
| Pyd-Peptide (MW > 1000) | <5% |
| Amino Acid Mixture | ~12% |

Example 5

Preparation of Pyridinoline-Coated Microplates

Biotin-labeled porcine albumin and a streptavidin-Pyd conjugate were utilized in the microplate coating. Biotinylation of the porcine albumin was carried out by adding 10 mg of biotin-X-2,4-dinitrophenol-X-L-lysine, succinimidyl ester (Molecular Probes) in 400 microliters of dimethylformamide to a 15 ml solution of PBS containing 150 mg of albumin. The mixture was allowed to react for two hours at room temperature, followed by G-25 column chromatography. Spectrophotometric analysis indicated four biotin molecules bound per mole of albumin.

Conjugation of N-Pyd (or H-Pyd) to streptavidin was accomplished by coupling a thiolated streptavidin to Pyd via the coupling agent, SMCC. Thiolated streptavidin was prepared by reaction with N-succinimidyl-3-(2-pyridylthio) propionate (SPDP, Pierce) as follows. To a 0.75 ml solution of 5 mg of streptavidin in PBS was added 21 uL of dimethylformamide containing 260 ug of SPDP. The mixture was allowed to react for one hour at room temperature, and then was dialyzed against PBS. The SPDP-labeled streptavidin was reduced by the addition of dithiothreitol to a final concentration of 10 mM. After incubation for one hour at room temperature, the thiolated streptavidin was purified on a G-25 column.

To form H-Pyd-streptavidin, a solution containing 180 ug of succinimidyl 4-(N-maleimidomethyl)cyclohexane-1-carboxylate (SMCC, Pierce) in dimethylformamide (4 ul) was added to a solution containing 0.5 mg thiolated streptavidin and 50 ug of H-Pyd in 100 µl of PBS. The mixture was allowed to react for 3 hours at room temperature and then was dialysed versus PBS. Spectrophotometric analysis of the resultant Pyd-streptavidin indicated between 1 and 2 equivalents of Pyd bound per equivalent of streptavidin.

Each of the wells in a 96-well ELISA plate were coated with N-Pyd as follows. To each well was added 150 microliters of biotin-albumin solution at 3.8 ug/ml in PBS, followed by an overnight incubation at 2°–8° C. The microplates were washed with PBS containing 0.3% "TWEEN"-20 and blocked by adding 200 ul of albumin at 1 mg/ml with an overnight incubation at room temperature. The microplates were then twice washed with PBS containing 0.05% "TWEEN"-20. The streptavidin-Pyd conjugate is immobilized via the streptavidin mediated binding to biotin. 150 ul of a solution containing streptavidin-Pyd at 100 ng/ml in PBS was added to each well of the biotin-albumin coated microplate. After a one hour incubation at room temperature, the plates are twice washed with PBS containing 0.05% "TWEEN"-20, and then incubated with 200 µL/well of 10% sucrose in 100 mM PBS for 2 hours to improve the stability of the support. After aspiration of the wells, residual liquid was then removed from the microplate by drying overnight in a convection oven at 37° C.

Example 6

Saliva Immunoassay

The following immunoassay was performed using the rabbit polyclonal antibodies characterized in Table 9 above (rabbit VI-8), and the N-Pyd coated microtiter plate described in Example 5.

N-Pyd standard solutions and saliva samples were tested in duplicate. The standard solutions consisted of 0 nM, 0.6 nM, 1.25 nM, 2.5 nM, 5.0 nM, 10 nM, and 20 nM N-Pyd in assay buffer (0.05% NaN$_3$ and 10% BSA in 10 mM sodium phosphate containing 150 mM NaCl, pH 7).

To a 200 µl aliquot of each standard solution or whole saliva sample (100 µl saliva mixed with 100 µl assay buffer) was added 20 µl of 50% v:v aqueous trichloroacetic acid (TCA). The resultant mixtures were vortexed briefly and centrifuged at 10,000 rpm for 5 minutes. The supernatant was collected (100 µl) from each centrifuge tube and mixed with 300 µl of 100 mM PBS.

Following addition of sample or standard to the wells (100 µl/well), 50 ul/well of VI-8 antiserum diluted 7,500-fold in assay buffer was added, and the assay plate was incubated at 4° C. overnight. After the plate was washed 3 times with 300 µl/well of wash buffer, 150 µl/well of goat anti-rabbit IgG-alkaline phosphatase conjugate (1:1000 dilution in assay buffer) was added, and the plate was incubated at room temperature for 1 h. The wells were then washed 3 times with wash buffer.

To each well was added 150 uL of enzyme substrate solution (2 mg/mL of p-nitrophenylphosphate (Sigma) in 1.0M diethanolamine, pH 9.8, containing 1 mM $MgCl_2$). Following a 1 hour incubation at room temperature, 50 µl of 3.0N NaOH was added to each well to stop the enzymatic reaction. The optical density at 405 nm was then measured with a Vmax reader (Molecular Devices Corp.).

The optical density readings (405 nm) from duplicate samples were averaged, and the averaged readings from the N-Pyd standards were used to construct a standard curve of OD reading vs. N-Pyd concentration. From this curve, the free N-Pyd crosslink concentration in each sample was determined.

Example 7

Binding Selectivity of Antibodies

N-Pyd, N-Dpd, and pyridinium-peptides (MW>1000) were isolated from urine samples as described in Example 1. Aliquots of the various pyridinium crosslink preparations were hydrolysed to convert the crosslinks in the fractions to H-Pyd and H-Dpd. The concentrations of Pyd in the N-Pyd and H-Pyd preparations, of Dpd in the N-Dpd and H-Dpd preparations, and of Pyd and Dpd in the pyridinium-peptide preparation, were determined by HPLC (Black et al., 1988). In addition, an amino acid solution containing an equimolar mixture of the 20 common amino acids, 150 µM each in PBS, was prepared.

Aliquots (50 µl) of the native crosslink preparations and the amino acid mixture were added in duplicate to Pyd-coated microtitre wells, and each well was assayed for pyridinoline as in Example 6. The optical density readings (405 nm) from duplicate samples were averaged, and from these values, the apparent N-Pyd concentration of each sample was determined using a standard curve established with purified N-Pyd. The percent reactivity of each sample was calculated as a ratio of apparent concentration (measured using the N-Pyd standard curve above) to total Pyd crosslink concentration in the sample determined by HPLC for total H-Pyd (times 100). The relative reactivity determined for purified N-Pyd was arbitrarily set at 100%, and the reactivities of the other crosslink preparations (and the amino acid mixture) were expressed as a percentage of 100.

Although the invention has been described with respect to specific embodiments and examples, it will be appreciated that various changes and modifications may be made without departing from the invention.

It is claimed:

1. A method of screening for the presence of a periodontal disease condition in a human subject, comprising obtaining an oral fluid sample from the subject, determining a level of pyridinium crosslinks selected from the group consisting of native peptide-free pyridinoline, native peptide-free deoxypyridinoline, or both, in the sample, and comparing the level determined with a predetermined level characteristic of normal subjects, where an above-normal level in the sample is an indication that the subject has a periodontal disease condition.

2. The method of claim 1, wherein the oral fluid is whole saliva.

3. The method of claim 1, wherein the oral fluid is gingival crevicular fluid.

4. The method of claim 1, wherein the selected crosslinks are native peptide-free pyridinoline.

5. The method of claim 1, wherein the selected crosslinks are native peptide-free deoxypyridinoline.

6. The method of claim 1, wherein the selected crosslinks are native peptide-free pyridinoline and native peptide-free deoxypyridinoline.

7. The method of claim 1, wherein said sample level is determined by immunoassay using antibodies specific for the selected crosslinks.

8. The method of claim 7, wherein said antibodies are monoclonal antibodies.

9. The method of claim 7, wherein said antibodies are polyclonal antibodies.

10. The method of claim 1, for use in monitoring a change in the status of periodontal disease in the subject, in response to a therapeutic treatment, which further includes determining the level of said pyridinium crosslinks in an oral fluid sample from the subject during or after such treatment.

11. The method of claim 1, which further includes the steps of (i) obtaining a salivary ductal sample from the subject, (ii) determining the level of such selected crosslinks in the ductal sample, and (iii) comparing the determined ductal level with a predetermined ductal level characteristic of normal subjects, where an above-normal ductal level is an indication that the subject has a bone resorption condition rather than a periodontal disease condition.

12. A method of screening for the presence of a bone resorption condition in a human subject comprising obtaining a salivary ductal sample from the subject, determining a level of pyridinium crosslinks selected from the group consisting of native peptide-free pyridinoline, native peptide-free deoxypyridinoline, or both, in the sample, and comparing the level determined with a predetermined level characteristic of normal subjects, where an above-normal ductal level is an indication that the subject has a bone resorption condition.

13. The method of claim 12, wherein the bone resorption condition that is screened for is osteoporosis.

14. The method of claim 12, wherein the selected crosslinks are native peptide-free pyridinoline.

15. The method of claim 12, wherein the selected crosslinks are native peptide-free deoxypyridinoline.

16. The method of claim 12, wherein the selected crosslinks are native peptide-free pyridinoline and native peptide-free deoxypyridinoline.

17. The method of claim 12, wherein said sample level is measured by immunoassay using antibodies specific for the selected crosslinks.

18. The method of claim 17, wherein said antibodies are monoclonal antibodies.

19. The method of claim 17, wherein said antibodies are polyclonal antibodies.

20. The method of claim 12, for use in monitoring a change in the status of a bone resorption condition in the subject, in response to a therapeutic treatment, which further includes measuring the level of said pyridinium crosslinks in a salivary ductal sample from the subject during or after such treatment.

* * * * *